(12) United States Patent
Chang et al.

(10) Patent No.: US 10,098,895 B2
(45) Date of Patent: *Oct. 16, 2018

(54) TREATMENT OF SYMPTOMS RELATED TO NEURODEGENERATIVE DISORDERS THROUGH PHARMACOLOGICAL DERMAL ACTIVATION OF CRANIAL NERVES

(71) Applicant: GLIA, LLC, Boston, MA (US)

(72) Inventors: Wei-wei Chang, Boston, MA (US); Kenneth I. Sawyer, Cushing, ME (US)

(73) Assignee: GLIA, LLC, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/695,376

(22) Filed: Sep. 5, 2017

(65) Prior Publication Data

US 2018/0064728 A1  Mar. 8, 2018

Related U.S. Application Data

(60) Provisional application No. 62/384,458, filed on Sep. 7, 2016.

(51) Int. Cl.
| | | |
|---|---|---|
| *A01N 45/00* | (2006.01) | |
| *A61K 31/56* | (2006.01) | |
| *A61K 31/57* | (2006.01) | |
| *A61K 31/568* | (2006.01) | |
| *A61K 31/352* | (2006.01) | |
| *A61K 9/00* | (2006.01) | |

(52) U.S. Cl.
CPC ............ *A61K 31/57* (2013.01); *A61K 9/0014* (2013.01); *A61K 31/352* (2013.01); *A61K 31/568* (2013.01)

(58) Field of Classification Search
None
See application file for complete search history.

(56) References Cited

U.S. PATENT DOCUMENTS

| | | |
|---|---|---|
| 9,056,857 B2 | 6/2015 | Zhu et al. |
| 2003/0195588 A1 | 10/2003 | Fischell et al. |
| 2009/0131385 A1 | 5/2009 | Voskuhl |
| 2010/0105646 A1 | 4/2010 | Brinton et al. |
| 2011/0077239 A1 | 3/2011 | Knipper et al. |
| 2012/0258132 A1 | 10/2012 | Blumenfeld et al. |
| 2014/0228438 A1 | 8/2014 | Iuvone et al. |
| 2014/0357686 A1 | 12/2014 | Crews |
| 2015/0045388 A1 | 2/2015 | Aung-Din |
| 2016/0030333 A1 | 2/2016 | Sawyer et al. |
| 2016/0095758 A1 | 4/2016 | Haire et al. |
| 2016/0338974 A1* | 11/2016 | Aung-Din .............. A61K 31/05 |

FOREIGN PATENT DOCUMENTS

| | | | |
|---|---|---|---|
| WO | WO-2008/070728 A2 | 6/2008 | |
| WO | WO 2014152385 A2 * | 9/2014 | ........... A61K 31/352 |
| WO | WO-2015/013252 A1 | 1/2015 | |

OTHER PUBLICATIONS

Kuo et al., "Electric stimulation of the ears ameliorated learning and memory impairment in rats with cerebral ischemia-reperfusion injury," Scientific Reports, received Aug. 17, 2015.*

* cited by examiner

*Primary Examiner* — Jared Barsky
(74) *Attorney, Agent, or Firm* — Cesari and McKenna, LLP

(57) ABSTRACT

A method for treating a symptom of a neurodegenerative condition. The method includes topically administering a composition that contains a sex steroid or a cannabinoid or a mixture of both to the forehead, to an area of the outer ear of the subject not including the ear canal, or to both of these anatomical locations. The symptom treatable by the method is a motor symptom or a non-motor symptom.

16 Claims, 2 Drawing Sheets

TREATMENT OF SYMPTOMS RELATED TO NEURODEGENERATIVE DISORDERS THROUGH PHARMACOLOGICAL DERMAL ACTIVATION OF CRANIAL NERVES

CROSS-REFERENCE TO RELATED APPLICATIONS

The present application claims the benefit of U.S. Provisional Patent Application Ser. No. 62/384,458, which was filed on Sep. 7, 2016, the content of which is hereby incorporated by reference in its entirety.

BACKGROUND

Technical Field

The present invention relates to the treatment of motor and non-motor symptoms related to neurodegenerative disorders through pharmacological dermal activation of one or more cranial nerves. In particular the trigeminal, facial, glossopharyngeal, vagus, and hypoglossal, and vestibulocochlear nerves are activated pharmacologically by non-invasive neural signaling to access the regions of the brain and brainstem integral to manifestation of the motor and non-motor symptoms of neurodegenerative conditions.

Background Information

Description of Neurodegenerative Disorders

Neurodegenerative disorders have both motor and non-motor components. Tremor is a typical motor symptom. "Tremor is an unintentional, rhythmic muscle movement involving to and fro movements (oscillations) of one or more parts of the body. It is the most common of all involuntary movements and can affect the hands, fingers, arms, head, face, voice, trunk, and legs. Most tremors occur in the hands." (National Institute of Neurological Disorders and Stroke 2012). Neurodegenerative disorders that have tremors as a component include Parkinson's disease, essential tremor, Lewy body dementia, multiple sclerosis, frontotemporal dementia, stroke, and traumatic brain injury. Tremors can be differentiated by frequency, amplitude, and when it is exhibited, i.e. resting, postural, or action (kinetic and/or isometric). Tremor differentiation is an important part of disease diagnosis.

Tremor is caused by abnormal changes to brain regions that innervate muscles. There may be multiple causes to these changes, such as disease, trauma, drug or genetic. Here we concern ourselves with neurodegenerative disorders where the symptoms and signs progress over time. Other functions including motor, non-motor, and cognitive, may be affected due to the brain changes and damage.

Parkinson's disease is a progressive and chronic neurodegenerative brain disorder that affects over 1 million people in the United States (FDA 2016). The presence of at least two of the following motor symptoms provides a presumptive diagnosis: resting tremor, bradykinesia (slowed movement), rigidity (dystonia), and postural instability. Other motor and physiological symptoms include kinetic tremor, uncontrolled movement (dyskinesia), restless leg, freezing, impaired balance and coordination, constipation, urinary incontinence and urgency, swallowing difficulty, olfactory dysfunction, weight loss, hypertension, shortness of breath, pain, excessive sweating, cramping and muscle aches. Non-motor symptoms may include cognitive impairment, mood disorders, sleep disturbances, speech difficulties, handwriting problems, visual disturbances, loss of short term or long term memory, impaired comprehension, apathy, impulsivity, depression, anxiety, and fatigue. An area of the brain called substantia nigra has been found to be associated with Parkinson's in progressive loss of neurons that is in turn related to dopamine deficiency (Jellinger, 2002). Lewy bodies consisting of alpha-synuclein are found to accumulate in these neurons.

Lewy body dementia is another example of a neurodegenerative disorder that presents initially with memory impairments, cognitive dysfunction, visual hallucinations, sleep disorders, depression, autonomic dysfunction, repeated falls, hallucinations, and delusions. A major differentiation from Parkinson's is that in LBD motor symptoms appear later than cognitive deficits, whereas in Parkinson's, motor symptoms appear first and cognitive symptoms appear later, and may not be noticeable until 12 months later. It affects approximately 1.4 million people in the U.S. (Lewy Body Dementia Association), is second only to Alzheimer's in dementia. One study showed more pronounced cortical atrophy than Parkinson's disease dementia (Seppi et al., 2007). MRI shows more preservation of the medial temporal lobes and hippocampal structures than with Alzheimer's (Farlow et al., 2016). Lewy bodies are found both inside and outside the substantia nigra, in deep cortical layers throughout the brain, especially in the anterior frontal and temporal lobes, the cingulate gyrus, and the insula. As in Parkinson disease, Lewy bodies in DLB can also be seen in the substantia nigra and locus ceruleus, as well as the raphe nuclei, nucleus basalis of Meynert, and other brainstem nuclei. Neuronal loss in DLB is found in the frontal lobes, nucleus basalis of Meynert, substantia nigra, and locus ceruleus. Synaptic density may also be reduced in the remaining neurons (Imamura et al., 1999).

Essential tremor is the most common tremor disorder affecting about 10 million people in the U.S. Tremor is the main symptom in ET, affecting hands, head, and voice, and possibly legs, trunk, and even internally. Essential tremor can affect all ages. It is believed to be an inherited disorder (International Essential Tremor Foundation 2012). The tremors are usually postural or action (both kinetic and isometric). Non-motor symptoms can include mild cognitive impairment, apathy, depression, anxiety, sleep disturbances. An underlying abnormality of the cerebellum and/or its pathways is the postulate (Benito-Leon et al., 2016).

Multiple sclerosis's common symptoms include sensory symptoms in the limbs or one side of the face, visual loss, acute or subacute motor weakness, diplopia, gait disturbance and balance problems, Lhermitte sign (electric shock like sensations that run down the back and/or limbs upon flexion of the neck), vertigo, bladder problems, limb ataxia, acute transverse myelitis, and pain (Richards R G et al. 2002). Non-motor symptoms may consist of depression, fatigue, and memory impairment. Pathogenesis involves inflammation, demyelination, and axonal degeneration (Dendrou et al., 2015). Lesions are located in the optic nerves, spinal cord, brainstem, cerebellum, and the juxtacortical and periventricular white matter (Popescu et al., 2012). In addition, demyelinated lesions can also be found in the corpus callosum (Barnard et al., 1974) and cortical gray matter (Calabrese et al., 2010; Lucchinetti et al., 2011).

Dystonia comprises various forms that can be differentiated from Parkinson's disease. Tremor is an important clinical feature in dystonia (Pandev et al., 2016). Dystonic tremors can also be differentiated from essential tremor as they occur in conjunction with other dystonic symptoms.

Amyotrophic lateral sclerosis is a rapidly progressive neurodegenerative disease that may present with weakness of the extremities or bulbar findings of dysarthria or dysphagia. Both upper motor neurons and lower motor neurons are involved. Death in about 3 years usually is from respiratory difficulties.

Other related movement disorders include ataxia, Huntington's disease, multiple system atrophy, myoclonus, progressive supranuclear palsy, Rhett syndrome, spasticity, and Tourette syndrome.

A major motor function disorder common to all neurodegenerative disorders is dysfunction of ocular gland secretion or ocular surface disease. Symptoms include dryness, grittiness, eye pain, hyperemia, photophobia, blurriness, and excessive tearing. Chronic graft-versus-host-disease is a common occurrence in allogeneic hematopoietic cell transplant. A major neurodegenerative result is mucocutaneous disorder that affects the skin, mouth, liver, lung, eye, and gastrointestinal tract. The manifestations of ocular symptoms resemble those of ocular dysfunction of other neurodegenerative disorders.

Herpes ophthalmicus or shingles, due to either reactivation of varicella-zoster or herpes simplex virus, distributes rash via cranial nerve V trigeminal to the eye and ocular adnexa. Besides painful vesicular rash, ocular symptoms and signs include pain, corneal epithelia defects, decreased corneal sensation, ocular inflammation, eyelid closure problems, and high intraocular pressure. Facial paralysis may also accompany other signs.

Herpes oticus ophthalmicus is the manifestation of the inner, middle, and external ear. There may be severe facial paralysis. Cranial nerve VII facial and VIII vestibulocochlear are involved. Signs and symptoms include painful blisters in and around the ear, the face, mouth and/or tongue, vertigo, nausea, vomiting, hearing loss, tinnitus, eye pain, alterations in taste, inability to close eyelid.

Current Treatment of Motor and Non-motor Related Symptoms

Treatments for motor movement symptoms currently range from systemic pharmacological to electrical stimulation, acupuncture, or surgical or ultrasound thalamotomy. No treatment currently resolves tremor or other motor and non-motor symptoms completely or prevents the disorder or progression. All current treatments are systemic or invasive, and are relatively high dose. Current pharmacological treatments cause many side effects, and many times there is increasing tolerance to dosing, as most of the administered treatments are not aimed specifically at neural targets.

Carbidopa-levodopa (Sinemet, Duopa, Rytary) remains the mainstay of treatment for the signs and symptoms of Parkinson's disease. Other treatments include drugs such as dopamine agonists (Requip-ropinirole, Mirapex-pramipexole, Apokyn-apomorphine, Neupro-rotigotine), COMT (catechol-O-methyltransferase) inhibitors, anticholinergics, and MAO-B (monoamine oxidase type B) inhibitors (Azilect-rasagiline, Deprenyl-selegiline). Deep brain stimulation is also a potential therapeutic option for patients with advanced Parkinson's disease and essential tremor. Non-pharmacological management approaches include exercise, yoga, meditation, diet, and lifestyle modification. Side effects with carbidopa-levodopa may include severe dyskinesia and other symptoms similar to the disease being treated. Reduced efficacy over time has been experienced. Dopamine agonists may be involved with sleep attacks, impulsive behavior, feet swelling, Surgical and non-invasive thalamotomy has been an alternative for reduction of motor symptoms when medications fail. It is now not a commonly used procedure. It may be used to treat severe tremor on one side of the body (most often in an arm or leg), but does not help with slow movement (bradykinesia), speech problems, or walking difficulties.

Deep brain stimulation (DBS) that involves implantation of an electrical stimulator targeting the subthalamic nucleus (STN) and the globus pallidus interna (GPi), may give significant improvement in dyskinesia in some, but may lead to other issues, such as discomfort with the device, loss of smell and cognitive issues. DBS also carries risks related to electromagnetic interference and debilitation (e.g. inability to speak).

Electrical stimulation has limited efficacy due to many variables, e.g., dose amplitude, pulse rate, and site of location, and does not address the complexity of neural synaptic interactions. It is believed that deep brain stimulation does not restore normal basal ganglia functions, but replaces those that have become abnormal. (Wichmann et al., 2016)

Essential tremor symptoms may be treated with beta blockers (in particular propranolol) or anticonvulsant drugs (in particular primidone). Other beta blockers and anticonvulsants are also used, as well as benzodiazepines, nimodipine, and botulinum toxin. Efficacy declines with time. If medications fail to control symptoms, the condition may also be treated with surgery (thalamotomy) or deep brain stimulation or ultrasound ablation of the thalamus.

Treatments for dystonia are similar to those used for the above tremor related disorders.

Current Lewy body dementia (LBD) treatment is similar to those used for Alzheimer's disease due to the greater cognitive deficit component in LBD. Cholinesterase inhibitors (ravastigmine and donepezil) have had varied success. Memantine and neuroleptics have had limited success.

Current treatments for multiple sclerosis are immune modulating agents that do not address tremor should it exist. Nonmedical options are used when severe tremor is involved.

There is no effective treatment for amyotrophic lateral sclerosis. Riluzole can only prolong survival by a short period.

Antimicrobial agents (e.g., anti-bacterial and anti-viral agents), corticosteroids, intraocular pressure lowering agents, and bandage lenses help to ease the signs and symptoms of herpes ophthalmicus and herpes oticus, but may not address chronic ocular and otic damage and motor symptoms such as facial paralysis.

There is no existing treatment for chronic ocular graft-versus-host disease. Palliative measures do not provide satisfactory relief.

In summary, current treatments for motor and non-motor signs and symptoms of neurodegenerative disorders are either lacking or involve high doses of medications not optimally targeted to the disorder and have undesirable side effects due to lack of specificity toward neural targets, and may even be risky as in the case of electrical deep brain stimulation, ultrasound, or surgical thalamotomy.

The need exists for improved, non-invasive pharmacological treatments for symptoms of neurodegenerative disorders that lack the drawbacks mentioned above.

SUMMARY

To meet this need, a method for treating a symptom of a neurodegenerative condition is provided. The method is carried out by topically administering a composition that contains a sex steroid, a cannabinoid, or a mixture thereof to the forehead, to an area of the outer ear of the subject not including the ear canal, or to both of these anatomical locations The symptom treatable by the method is a motor symptom or a non-motor symptom.

The details of one or more embodiments are set forth in the description, the drawings, and the examples below. Other features, objects, and advantages will be apparent from the detailed description of several embodiments and also from the claims.

Importantly, all publications and patent documents cited herein are hereby incorporated by reference in their entirety.

BRIEF DESCRIPTION OF THE DRAWINGS

The invention description below refers to the accompanying drawings, of which.

DETAILED DESCRIPTION

Figure 1:
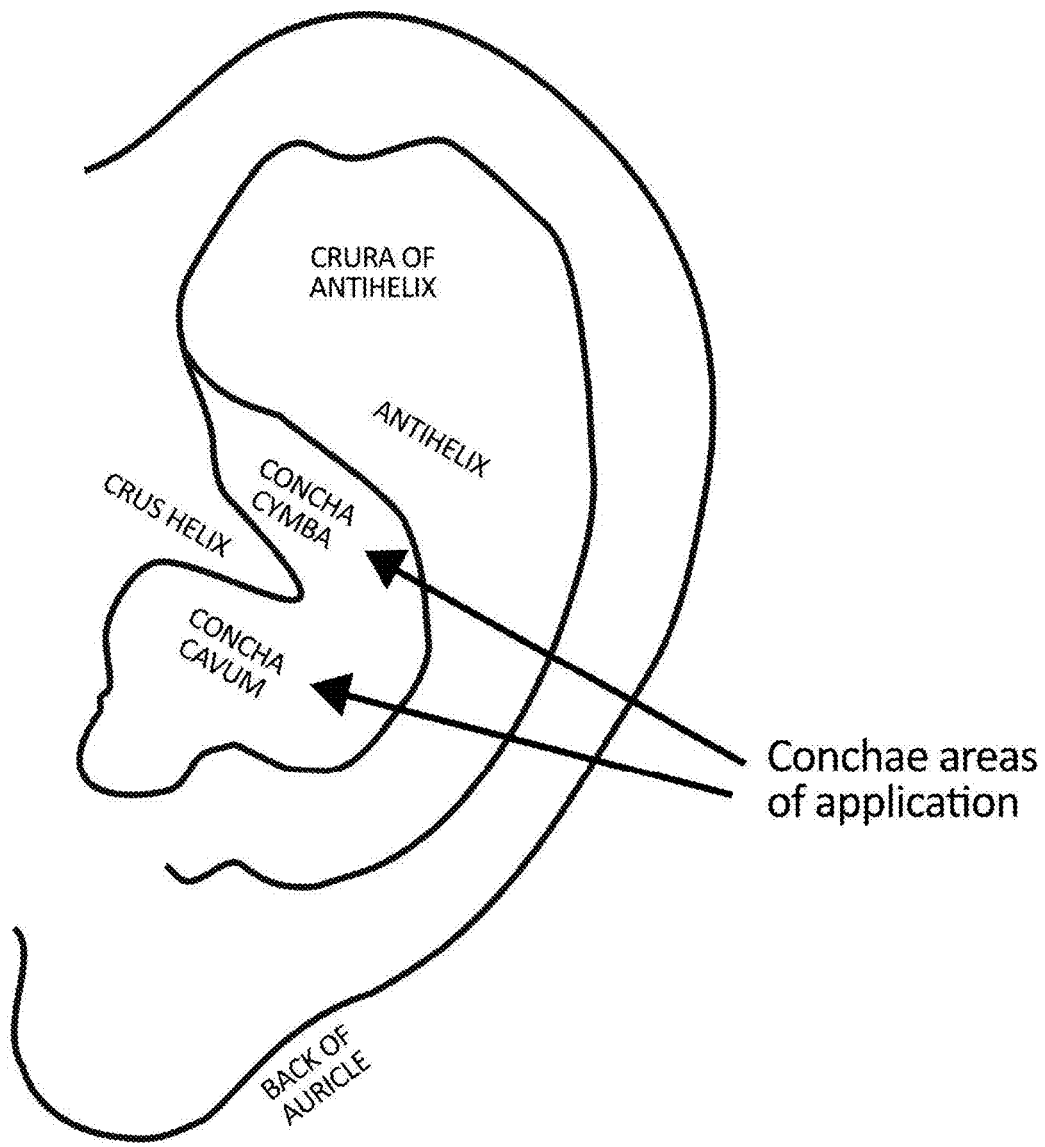
FIG. 1 is a diagram of anatomical sites of the ear for topical administration of a composition for treating a symptom of a neurodegenerative disorder.

Pharmacological agents are formulated in various topical formulations such as gels, creams, liquids, sprays, patches, and delivered by any method that provides access to specific areas of skin, including topical, intradermal, subcutaneous, intramuscular, or via topical implants. In these skin areas or sites, keratinocytes of epidermis provide access to cranial nerves, in particular but not to exclude others, the trigeminal (CN V), facial (CN VII), glossopharyngeal (CN IX), the vagus (CN X), and hypoglossal (CN XII). There are 12 pairs of cranial nerves in humans. Each has either sensory (afferent), motor (efferent) or mixed (sensory and motor) functions. There are intercommunications between and among the cranial nerves. The 5 cranial nerves named here are critical to the surprising finding that exposing certain peripheral skin sites to pharmacological agents can treat motor and non-motor symptoms of neurodegenerative disorders. Not to be bound by theory, one possible mechanism is that the pharmacological agents penetrate the stratum corneum to the epidermis, bind to specific receptors there to activate signaling to brain areas, thereby restoring homeostasis, but the agents do not themselves migrate to those areas.

Cranial nerves III to XII all traverse the brainstem. The ophthalmic, maxillary and mandibular branches of the trigeminal nerve (CN V) convey sensory afferent signals to the brain areas via the brainstem to activate efferent motor functions and parasympathetic innervation via the facial nerve (CN VII) to secretory glands of the eyes, nose, and mouth. The facial nerve conveys sensory signals through sensory nerves of the tongue, palate, and external meatus, and activates efferent motor functions and parasympathetic secretory glands. The glossopharyngeal nerve (CN IX) conveys sensation of taste from the tongue, and general sensation from the oropharynx, tongue, pharyngeal mucosa, and special sensation from carotid body and sinus, with motor efferents to the pharynx and tongue for speech and swallowing, and parotid gland saliva production and salivation. The vagus nerve is the largest nerve and is associated with all major organ functions of the body including respiratory, cardiac, gastrointestinal, and urinary. There is sensory afferent input from all the organs, vagal stimulation in turn affects the function of the same organs. The hypoglossal nerve controls speech and swallowing via muscles of the tongue. There is cross communication between the cranial nerves, much of it in the brainstem where the nerves traverse: trigeminal (CN V) within spinal trigeminal nucleus; facial (CN VII) within facial nucleus, superior salivatory nucleus, solitary nucleus, and spinal trigeminal nucleus; glossopharyngeal (CN IX) within spinal trigeminal nucleus and solitary nucleus; vagus (CN X) within dorsal motor nucleus, nucleus ambiguus, spinal trigeminal nucleus, and solitary nucleus; and hypoglossal (CN XII) within hypoglossal nucleus. It is within these nuclei in the brainstem that the various nerves can communicate directly with each other. The technology of the current invention utilizes the cross-communication between these nerves to achieve the observed effects.

Disclosed is that there are several peripheral areas of the skin on the head and neck, excluding the palpebral area of the face and the ear canal, where the nerves can be accessed effectively and efficiently by pharmacological agents. In particular, nerves can be accessed via the forehead and facial areas, excluding the palpebral, via the outer ear (conchae, external meatus, back of the ear), and via back of the neck. These sites also complement each other, confirming the cross-communication and overlap of the different nerves. It is known that the keratinocytes of the epidermis contain receptors for many compounds (Zouboulis CC 2004). One likely scenario is that when compounds bind to their specific receptors signaling of the nerves result that sets up electric potential. Forehead applications of chemical agents signal the trigeminal nerve that in turn innervates parasympathetic tear film secretions via the facial nerve branch greater petrosal nerve that synapses in pterygopalatine ganglion. The ear applications access the auricular branch of the vagus nerve that carries the stimulus to the jugular ganglion, then the vagus nerve into the medulla oblongata, part of the brainstem, to the nucleus of the solitary tract, the spinal trigeminal nucleus, nucleus ambiguous, and dorsal motor nucleus. Emanating from this region is the control of multiple vagal functions including respiratory, cardiac, gastrointestinal, and urogenital.

Additional findings are that very small doses in contrast to what is required in systemic delivery are required once or twice daily, but the pharmacological agents must be applied in such a manner, and from specified formulations, so that they penetrate to the epidermis. It is unnecessary to go deeper than the epidermis, or to be absorbed into the blood circulation. Thus there are no blood brain barrier issues. It is also the finding that once the agents have been applied, the activation produces both a surprisingly rapid and sustained efficacy. The activation appears to be remote and not proximate innervation by the agents themselves. A further finding is that there has been no buildup of tolerance after months and years of use.

Additional surprising findings of the invention are that multiple pharmacological agents can be effective for the treatment of tremor and other motor and related non-motor symptoms. Synthetic versions of endogenously available agents that have receptors residing in keratinocytes have been found to be active. Examples are neurosteroids such as progesterone, and cannabinoids such as tetrahydrocannabinol.

Another finding is that the pharmacological agents by this method may reduce or eliminate tremor and other motor and non-motor side effects created by concomitantly administered systemic drugs. This in fact changes the therapeutic profile of existing systemic agents.

As mentioned above, the method of the invention includes topically administering a composition that contains a sex steroid, a cannabinoid, or a mixture of both to the outer ear of the subject. For example, the composition can be administered to the concha cymba, concha cavum, antihelix, crus helix, crura of antihelix, intertragal notch, and the dorsal surface of the auricle. See FIG. 1.

In a particular example, the composition is administered to the concha cymba of both ears of the subject.

Figure 2:
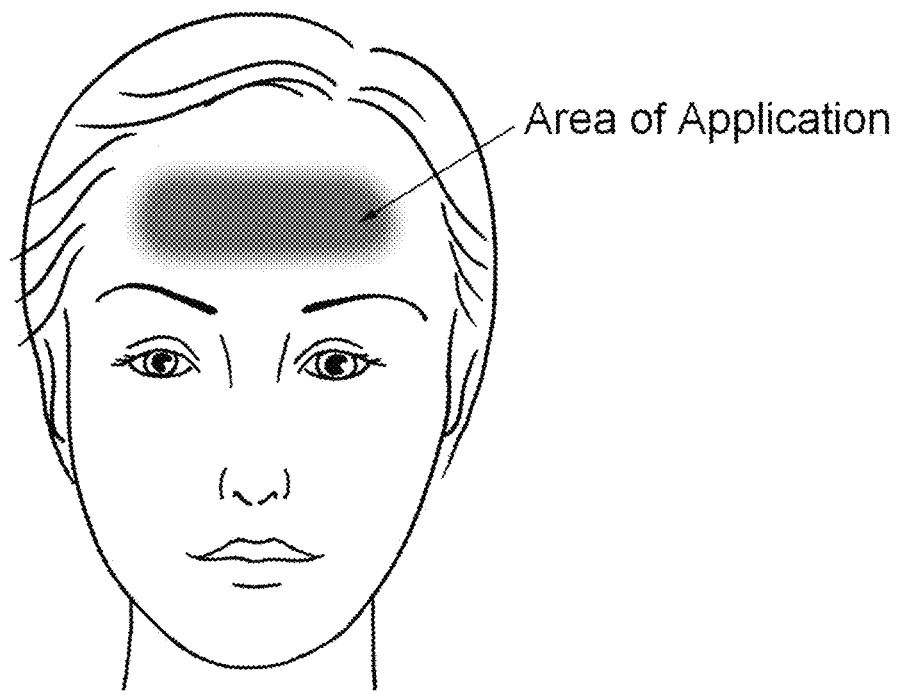
FIG. 2 is a diagram of anatomical sites of the forehead for topical administration of a composition for treating a symptom of a neurodegenerative disorder.

The method of the invention also encompasses administering the composition topically to an area of the forehead of the subject, in combination with administration to the outer ear described above. The forehead includes an area of the head bounded by the hairline, the supraorbital ridge, and the temporal ridges. See FIG. 2.

Furthermore, the composition can be topically administered to three sites, namely, the forehead, the right ear, and the left ear.

In one example of the method, the composition is administered once per day. In another example, the composition is administered more than once per day, e.g., two times per day, three times per day, and four times per day. In a preferred method, the composition is administered once or twice per day.

Administration of the composition is effective for treating one or more symptom of a neurodegenerative disorder for a period of 8 to 24 hours, e.g., 8, 10, 12, 16, 20, and 24 hours.

As mentioned above, the composition for administering to the outer ear or to the forehead can contain a sex steroid. The sex steroid can be, but is not limited to, estrogen, androgen, pregnenolone, allopregnanolone, testosterone, and progesterone. In an exemplary composition, a mixture of these compounds is included. In another exemplary composition, the sex steroid is progesterone. In yet another example, the sex steroid is testosterone. The composition can also contain both progesterone and testosterone.

The method encompasses administering the composition to provide a dose of 0.001 mg to 30 mg per day of the sex steroid, i.e., an effective amount, for treating a symptom of a neurodegenerative disease. For example, the dose of sex steroid in the topically applied composition can be 0.001 mg, 0.005 mg, 0.01 mg, 0.05 mg, 0.1 mg, 0.2 mg, 0.3 mg, 0.4 mg, 0.5 mg, 1 mg, 2 mg, 2.5 mg, 3 mg, 4 mg, 5 mg, 7.5 mg, 10 mg, 15 mg, 20 mg, 25 mg, and 30 mg per day.

The composition can contain the sex steroid in concentrations from about 0.001% by weight to about 80% by weight. For example, the concentration of sex steroid can be 0.001%, 0.005%, 0.01%, 0.05%, 0.1%, 0.25%, 0.5%, 1%, 2.5%, 5%, 10%, 20%, 25%, 50%, 75%, and 80%.

Any of the sex steroids described supra, can be formulated with appropriate excipients known in the art. The composition containing the sex steroid can be, e.g., a liquid or semi-solid, a solution, a suspension, an emulsion, a gel, a cream, a lotion, an ointment, or a transdermal patch. The composition can include one or more pharmaceutical excipients containing a small amount of skin penetration enhancer, e.g., an alcohol, an amide, an ether, a glycol, and a hydrocarbon oil. Delivery can be simple or actively assisted by an electric current or other electrophysical device. For example, the sex steroid-containing composition can be administered by applying it to the outer ears and/or the forehead. Alternatively, the composition can be administered by iontophoresis or by subcutaneous or intradermal injection.

As set forth above, the composition for administering to the outer ear or the forehead can contain a cannabinoid. The cannabinoid can be, but is not limited to, dronabinol, cannabinol, cannabidiol, $\Delta^9$-tetrahydrocannabinol, $\Delta^8$-tetrahydrocannabinol, 11-hydroxy-tetrahydrocannabinol, 11-hydroxy-$\Delta^9$-tetrahydrocannabinol, levonantradol, $\Delta^{11}$-tetrahydrocannabinol, tetrahydrocannabivarin, anandamide, virodhamine, noladin ester, 2-arachidonoylglycerol, and nabilone.

In a preferred embodiment, the cannabinoid is $\Delta^9$-tetrahydrocannabinol. In a particularly preferred embodiment, the cannabinoid is dronabinol.

Dronabinol, as used herein, refers to a pure isomer of $\Delta^9$-tetrahydrocannabinol, namely, (−)-trans-$\Delta^9$-tetrahydrocannabinol, also known as (6aR,10aR)-6a,7,8,10a-tetrahydro-6,6,9-trimethyl-3-pentyl-6H-dibenzo[b,d]-pyran-1-ol.

The method encompasses administering the composition to provide a dose of 0.001-10 mg per day of the cannabinoid, i.e., an amount that is effective for treating a symptom of a neurodegenerative disease. For example, the dose of cannabinoid topically applied can be 0.001 mg, 0.005 mg, 0.075 mg, 0.01 mg, 0.02 mg, 0.03 mg, 0.04 mg, 0.05 mg, 0.075 mg, 0.1 mg, 0.2 mg, 0.25 mg, 0.3 mg, 0.4 mg, 0.5 mg, 0.75 mg, 1 mg, 1.5 mg, 2 mg, 2.5 mg, 5 mg, 7.5 mg and 10 mg per day.

The composition can contain the cannabinoid in concentrations from about 0.001% by weight to about 80% by weight. For example, the concentration of cannabinoid can be 0.001%, 0.005%, 0.01%, 0.05%, 0.1%, 0.25%, 0.5%, 1%, 2.5%, 5%, 10%, 20%, 25%, 50%, 75%, and 80%.

Any of the cannabinoids, like the sex steroids described, supra, can be formulated with appropriate excipients known in the art. The composition containing the cannabinoid can be, e.g., a liquid or semi-solid, a solution, a suspension, an emulsion, a gel, a cream, a lotion, an ointment, or a transdermal patch. The composition can include one or more pharmaceutical excipients containing a small amount of skin penetration enhancer, e.g., an alcohol, an amide, an ether, a glycol, and a hydrocarbon oil. Delivery can be simple or actively assisted by an electric current or other electrophysical device. For example, the cannabinoid-containing composition can be administered by applying it to the forehead. In an alternative embodiment, the composition can be administered by iontophoresis or by subcutaneous or intradermal injection to the forehead.

In one example, the method includes administering a composition that contains both a sex steroid and a cannabinoid. In another example, the method includes administering one composition containing a sex steroid and another composition containing a cannabinoid. In yet another example, one composition contains two sex steroids, e.g., testosterone and progesterone, and another composition contains a cannabinoid, e.g., dronabinol.

As mentioned, supra, the method of the invention encompasses administering the composition topically to the right outer ear, the left outer ear, the forehead, and any combination of these three sites. If more than one site is used, the composition is divided equally between those sites. For example, if an amount of the composition that contains 0.75 mg of a sex steroid is applied to both outer ears of a subject, the composition is applied in two separate portions, each of which contains 0.375 mg of the sex steroid. If the same composition is administered to all three sites, it is divided into three equal portions, each of which contains 0.25 mg of the sex steroid.

In a particular embodiment, the composition described above is administered concurrently or sequentially with providing electrical stimulation to the outer ear. The composition, which contains a sex steroid, a cannabinoid, or both, enhances the efficacy of the electrical stimulation. For example, administering the compositions set forth above can restore normal synaptic activity. Subsequent or simultaneous application of low level electrical stimulation can therefore have enhanced efficacy as compared to electrical stimulation alone, which does not restore normal synaptic activity.

The method of the invention is effective for treating one or more symptom of a neurodegenerative condition. The symptom can be a motor symptom or a non-motor symptom.

Non-limiting examples of a motor symptom include tremor of the hands, fingers, arms, head, neck, legs, feet, eyes, or eyelids, face mask, rigidity, loss of equilibrium and balance, foot shuffling, slowed movement, uncontrolled movement, loss of facial muscle control, drooling, face masking, facial palsy, reduced breathing, volume incapacity, gastroparesis, constipation, urinary frequency, urgency, incontinence, reduced tear film secretion, evaporative dry eye resulting from non-blinking, and blepharospasm, Turning to a non-motor symptom, it can be, but is not limited to, cognitive dysfunction, memory impairment, disorientation, inability to speak or understand, mental decline, failing or jumbled speech, executive function impairment, irritability, personality changes, restlessness, anxiety, mood swings, depression, apathy, impulsivity, paranoia, and hallucinations.

The method of the invention can treat iatrogenic motor and non-motor symptoms similar to those described above arising from the neurodegenerative disorder. Iatrogenic motor symptoms include, but are not limited to, abnormal gait, hyperkinesia, hypertonia, and worsening of tremors.

In a specific example, the method is used for treating iatrogenic symptoms caused by carbidopa-levodopa. Exemplary iatrogenic symptoms include restless muscle movements in the eyes, tongue, jaw, or neck; worsening of tremors; high fever; stiff muscles; sweating; fast or uneven heartbeats; rapid breathing; feeling faint; seizure (convulsions); painful or difficult urination; severe nausea, vomiting, or diarrhea; confusion, hallucinations, anxiety, agitation, depressed mood, suicidal thoughts; chest pain or heavy feeling, and pain spreading to the arm or shoulder.

In another specific example, the method is used for treating iatrogenic symptoms caused by rasagiline. Among these symptoms are hallucinations, dyskinesia, accidental injury, weight loss, postural hypotension, vomiting, anorexia, arthralgia, abdominal pain, nausea, constipation, dry mouth, rash, abnormal dreams, fall, asthenia, bundle branch block, gastrointestinal hemorrhage, abnormal gait, anxiety, hyperkinesia, hypertonia, neuropathy, tremor, increased coughing, hematuria, and urinary incontinence.

The method of the invention can be used for treating one or more symptoms of a neurodegenerative condition. Exemplary neurodegenerative conditions are Parkinson's disease, Lewy body dementia, essential tremor, multiple sclerosis, dyskinesia, dystonia, ataxia, Huntington's disease, multiple system atrophy, myoclonus, progressive supranuclear palsy, Rhett syndrome, spasticity, Tourette syndrome, amyotrophic lateral sclerosis, Bell's palsy, herpes ophthalmicus, herpes oticus, neurodegeneration due to chronic graft-versus-host-disease, and neurodegeneration due to viral and iatrogenic causes.

In a particular example, the above method is used for treating a subject who is already undergoing pharmacological, surgical, electrical stimulation, acupuncture, or ultrasound treatment for the neurodegenerative condition.

In yet another example, topically administering the composition retards progression of the neurodegenerative condition in addition to treating the symptoms thereof.

Without further elaboration, it is believed that one skilled in the art can, based on the disclosure herein, utilize the present disclosure to its fullest extent. The following specific examples are, therefore, to be construed as merely descriptive, and not limitative of the remainder of the disclosure in any way whatsoever.

EXAMPLES

Example 1

Male Parkinson's Disease Patient

A 78-year-old male was diagnosed with the early stages of Parkinson's disease in December of 2014. His symptoms included tremors in the hands, impaired short term memory, slow and uncontrolled rigid movements while walking and eating, and declining ocular blink function. The patient also had dry eyes with hyper-tearing, burning, and itching. A CT scan of head was unremarkable at this stage.

The patient was prescribed oral rasagiline for his Parkinson's disease which he began taking immediately.

The patient was also treated with progesterone 1% on the forehead initially once daily beginning in March 2015. This relieved his ocular symptoms of burning and itching. The progesterone was applied as needed for about a year.

His Parkinson's symptoms were stable for nearly one year after which the disease progressed rapidly with the following symptoms worsening significantly: (i) decline in cognitive function, (ii) poor short term memory, (iii) constant tremors in both hands, (iv) weakness, (v) depression, (vi) lack of motivation including inattention to routine personal hygiene, (vii) irritability, (viii) interrupted speech and difficulty finding words, (ix) social withdrawal, (x) dystonia, (xi) bradykinesia.

By this time, the patient was dependent on others for most of his needs.

He was seen by the prescribing neurologist on Jun. 9, 2016, who confirmed the progression of symptoms by physical examination. At this point the patient had also discontinued using progesterone for the eye.

The neurologist ordered a stop to rasagiline therapy and instead ordered carbidopa-levodopa 25/100 mg 3 times daily and 10 mg escitalopram for depression.

Instead of the prescribed regimen, the patient began dermal application of dronabinol 1.25 mg 2 times daily to three sites: (i) the forehead, (ii) the concha of the left ear, and (iii) the concha of the right ear. Each dose of 1.25 mg was divided equally between the three application sites. This treatment regimen began Friday Jun. 10, 2016 concurrent with the discontinuation of rasagiline.

The following changes were noted within three days of dronabinol treatment while the patient was still washing out of rasagiline: more fluid speech, less searching for words, fewer thought gaps, socially interactive with wife and stepson, initiated interactions, responsive to gestures, more centered and present in the moment, and more socially engaged.

His dry eyes resolved with no need for artificial tears which he had been applying multiple times per day. Consequently, eye rubbing behavior ceased. He experienced less brain fog and was more motivated to turn over in bed, rise up and out of his chair, walk, and get in and out of a car.

Two weeks after beginning treatment with dronabinol in the absence of other medications, the following symptoms improvement trends continued, and comparison to the prior three days was noted: persistent postnasal drip resolved, chest cough and asthmatic wheezing resolved, motivation improved, able and willing to perform personal hygiene without help, would get his own snacks, would get himself into and out of bed to use the restroom, would get up out of a chair to walk. He stopped depending on other people to do things for him. He had significantly less bodily rigidity as evidenced by improved walking, use of his hands and arms, ability to get in and out of a chair, a bed, and a car. He exhibited markedly reduced hand tremors. His motor skills and coordination improved including moving food from plate to his mouth at a normal pace. A decrease in facial masking was noted with more voluntary facial expression. His depression resolved in the absence of antidepressants. He was less irritable; had much improved memory function; and his voice was consistently stronger and vibrant.

On Jul. 11, 2016, the patient returned to his neurologist for an examination. At this time, the neurologist was told of the dronabinol treatment and that no other drugs, e.g., rasagiline and carbidopa-levodopa, had been taken for the past 30 days.

The doctor conducted a physical exam including rigidity, coordination, and movement in general. He also observed the patient's cognition, motivation, speech pattern, and lack of depression.

Generally all improved symptoms as noted above were confirmed by the doctor's examination. The doctor ordered him to continue dronabinol therapy. The doctor put a is hold on the carbidopa-levodopa treatment and all antidepressants.

On Jul. 27, 2016, the patient's wife reported a 90% improvement of his Parkinson's disease symptoms, including motor, cognitive, and emotional symptoms. She observed much less rigidity, increased talkativeness and social engagement, and saw no depression. Tremors have much improved in both hands and his dexterity had improved. Indeed, the patient was competent to install applications and navigate on a smartphone and tablet device without assistance.

The patient has been stable at the improved level described above during 3 months of dronabinol application to the conchae of the outer ears and forehead as the sole Parkinson's medication is stable. His neurologist has continued this treatment regimen.

From July 2016 to August 2017, the patient used progesterone 1% to the forehead applied once every week to fully manage dry eye disease symptoms associated with his Parkinson's disease. No artificial tears were necessary.

In February 2017, the patient, who suffers from debilitating moderate spinal stenosis, started taking Azilect (rasagiline) and carbidopa-levodopa to improve his walking and flexibility. Previously, his Parkinson's disease had remained stable on topical dronabinol applied to the forehead and ear conchae, showing improved cognition, emotional lability, social and personal hygiene skills, orientation in time and place, motivation, and speech. The patient decided that, together with the prescribed medications, he would switch from dronabinol to topical testosterone gel applied to the forehead and ear conchae to see if this would impact his longstanding low testosterone levels.

Prior to the switch, cognitive function and other nonmotor symptoms rapidly deteriorated during tapering-off of the dronabinol, even though the patient had already started taking the prescribed Azilect and carbidopa-levodopa. The prescribed medications provided some motor function improvement, in particular alternating sitting and standing modes, turning over in bed, and some improvement in walking without shuffling. Yet, his tremor while on the prescribed medications was no more improved than when he was applying dronabinol alone.

In March 2017, topical testosterone gel application was instituted as an adjunct to is the prescribed Azilect and carbidopa-levodopa. By the third day, the patient's wife reported an improvement in cognitive and non-motor symptoms, particularly in word recall, memory, fluidity of speech, self-motivation in daily hygiene, appetite, and an elevation in energy and mood.

The patient voluntarily stopped topical testosterone for 3 weeks in June 2017. Within 3 days, a significant decline in cognitive and emotional function was noted. At the end of 3 weeks, topical testosterone was re-instituted as an adjunct to the prescribed medications.

Throughout the course of neural cranial treatment with low dose dronabinol, progesterone, and/or testosterone, no adverse events were noted.

The patient's wife reported on his progress for the one-year period leading up to August 2017. She observed that the application of testosterone to the forehead and ears had a very positive impact on his mental stability. He showed improved cognitive function, increased alertness and motivation, improved verbal skills, interaction with others, mood, personal hygiene, and generally an overall improvement in function. When testosterone application was stopped, she saw a definite decline in his overall functioning. As soon as testosterone application was resumed after a three week hiatus, his overall functioning returned immediately to the improved levels. The tremors were not any worse and mobility was acceptable.

Example 2

Female Parkinson's disease subject

A 79-year-old female was diagnosed with Parkinson's disease in August of 2015. Notable symptoms include both resting and action tremor of the left hand and fingers, forearm, and, to a lesser extent, the right hand and the left leg. Handwriting and computer keyboard work were difficult. She had ocular symptoms associated with the disease, including dry eye disease with moderate to severe burning and grittiness, rapid blink rate, and partial blinking. She used artificial tears constantly in an attempt to alleviate the ocular symptoms. She had not been on any Parkinson's medications. Her Parkinson's tremor followed an "on-off" cycle that correlated with her stress levels, the "on" cycle being times with low stress and few symptoms, and the "off" cycle induced by stress showing an increase in symptoms.

In October 2016, the subject began applying progesterone 1% to her forehead and within the first week her dry eye disease resolved, with no need for artificial tears. There was no impact on the tremors. The addition of topical progesterone applied to the ear conchae also had minimal impact on tremor symptoms.

In late February 2017, the subject started applying single daily doses of 0.125% testosterone to the forehead and ear conchae. By the third day of treatment, the subject was tremor-free for periods of 4-6 hours, and the "on" part of the cycle was more frequent. Even when tremor was evident, the amplitude was less, and the tremors resolved sooner. In mid-March, the subject reported that she had gone two full days tremor-free and also reported increased strength and energy. The dose of testosterone was increased to 0.2% once daily in early April.

Through April 2017, she continued to report improved stress management, elevated mood with increase in libido and vaginal lubrication. Her self-reported improvement in physical strength and energy was confirmed by a personal trainer and a physical therapy masseuse. Her gait was spirited and she could skip without problems.

Regular neurological examinations by two different neurologists showed that her disease was non-progressive.

In July 2017, testosterone application was stopped after a taper to evaluate its effects. Her blood showed mildly elevated total and free testosterone for a female of her age. No negative side effects were reported by her or by her internist. By day 3 of testosterone abstinence, her tremors were more frequent with more "off" periods. In the 6 weeks that followed, the subject exhibited a downward trend in symptoms to pre-treatment levels, including increased tremor amplitude and frequency, mood drop, lower energy including libido, greater anxiety and pessimism about her disease, and a lower ability to cope with every day stress. Her dry eye disease continued to be well managed by topical progesterone. On Aug. 17, 2017, she reported extreme anxiety.

That same afternoon, the subject applied 0.2% testosterone to her forehead and ear conchae, and the next day reported less anxiety and more "on" cycles. By Aug. 20, 2017, she reported having stabilized on the once daily applications with a 60% or greater increase in "on" periods. On August 28, she reported going 9 hours without tremors and leg spasms. On Aug. 30, 2017, the subject was able to walk 8 miles and exercised in between. She described herself as feeling 100%.

Example 3

Parkinson's Tremor and co-morbid Ocular Graft-versus-host Disease

A 55-year-old male was diagnosed with Parkinson's disease over 3 years ago, leukemia about 2 years ago, and ocular graft versus host disease resulting from allogeneic stem cell treatment for the leukemia. The patient has been on oral carbidopa-levodopa for at least 2 years.

He was examined in June 2016 by an ophthalmologist for surface eye disease and was found to have no discernable tear film, filaments and inferior staining along with blepharospasm and blepharitis, and concomitant symptoms of burning and photophobia. The patient started treatment with twice daily progesterone 1% gel applied to the forehead to promote ocular secretion of tear film, and to resolve other symptoms and signs of surface eye disease. After initial treatment, the patient reported immediate relief of photophobia and burning, and tear film secretion was improved. On a follow up visit 5 weeks later, he reported continued relief from burning and photophobia.

When the patient was first seen in June 2016, he had noticeable significant tremors in both hands and multiple fingers. These were related to his Parkinson's disease as diagnosed and included muscle contractions, i.e., dyskinesia, related to his carbidopa-levodopa oral treatment. During the 5 weeks' of treatment with progesterone applied to the forehead, there was no change seen in the hand and finger tremors.

During the 5-week ophthalmologist follow-up visit, the progesterone treatment regimen was performed in the office in modified form. More specifically, the daily dose of progesterone was divided, with 1 mg applied to the concha of each ear, excluding the forehead, to which progesterone had been applied 6 hours earlier. The patient reported improved moisture and comfort in both eyes approximately 2 minutes post application. Surprisingly, the tremors in the hands and fingers were reduced by about 90% in frequency and amplitude simultaneously also at 2 minutes post application.

The patient had taken carbidopa-levodopa extended release medication at 6 am that morning, with an added immediate release dose at 8 am. The visit to the ophthalmologist was at 2 pm. At that point there was uncontrolled movement of the hands (dyskinesia) along with finger vibrations. The patient reported that the usual duration of efficacy of his carbidopa-levodopa regimen was 4 hours. Normally he would have taken another carbidopa-levodopa dose at 2 pm. Instead, progesterone was applied to the concha of both ears as described, supra.

The tremor resolution was stable for the remainder of the 1.5 hour office visit. The patient and his wife noted that he also achieved voluntary control over his hands and fingers.

Following the visit, the patient and his wife reported that he remained tremor-free until the subsequent visit 5 days later while the patient was on topical progesterone treatment using both conchae and forehead applications, while continuing on carbidopa-levodopa at a lower dosing frequency.

During the next office visit, his tremor continued to show improvement, as evidenced by greater control over his movements with less rigidity and more fluidity.

The patient's eyes continued to produce tear film and felt comfortable. His face showed less rigidity and more expression; facial expression and hand gestures became coordinated and interactive.

Example 4

Chronic Ocular Graft-versus-host Disease (GVHD)

A 64-year-old patient with chronic ocular GVHD, upon examination, had numerous ocular surface conditions as well as damaged Meibomian glands and ocular disease behind the eye. There was notable ocular surface disease including no visible production of tear film observed by Tearscope, profuse exudate in eyes, lid sticking, and recurring filamentary keratitis.

After 4 weeks of treatment with progesterone 1% to the forehead, tear film production was observed using the Tearscope, and a noticeable decrease in exudate was observed in both eyes. An improvement in lid sticking and friction were reported, as was overall comfort.

Example 5

Second Case of Chronic Ocular GVHD

A 55-year-old male patient with chronic ocular GVHD complained of eye discomfort, burning, and sticking lids. Upon examination, he was found to have right eye surface eye disease as evidenced by poor tear film secretion and rapid tear film breakup time on examination by Keratograph 5.

His first-measured tear film breakup time was 7.4 seconds, with an average breakup time of 11.39 seconds.

The patient was treated with a single dose of progesterone 1% to his forehead, followed by retesting of the tear film breakup time after 30 minutes. At that time, the first-measured tear film breakup time was 21.03 seconds, with an average breakup time of 21.35 seconds. The tear meniscus height in both eyes increased over 0.6 mm following the single application of progesterone.

The patient reported that applying progesterone twice a day to his forehead increased his ocular comfort for at least 5 hours with each dose.

Example 6

Third Case of Chronic Ocular GVHD

A 55-year-old male patient with chronic ocular GVHD was examined and found to have ocular surface disease in both eyes, including filamentary keratitis. Upon examination by Tearscope there was a lack of tear film production evident in both eyes along with pronounced filaments in the left eye.

He was treated with progesterone 1% to his forehead and re-examined 50 minutes later by Tearscope. This examination revealed the production of tear film in secretions in both eyes and consequent flushing of the filaments in the left eye. The patient reported improved comfort with the administration of the single dose of progesterone.

Example 7

Essential Tremor

A 62-year-old female developed persistent right hand tremors of a kinetic (non-resting) type that has been continuous over the past 6 years. The left hand had a very mild, hardly noticeable slight tremor. This condition had not worsened over time. There were no other symptoms or signs suggesting Parkinson's disease, dystonia, or Lewy body disease. Initially, her doctor thought that these symptoms were stress related and she has been taking 2.5 mg of escitalopram for over 6 years. Yet, there was no resolution of the tremor. The subject was not on hormone replacement therapy or any other medication.

Concomitantly, the subject suffered from uncomfortable eyes, with a sticky burning sensation and development of blurred vision after about 5-6 hours of contact lens wear. For the past 3 years, the subject was administered 1% progesterone gel (1 mg per day) by dermal application to the forehead once per night. The progesterone gel prolonged comfortable contact lens wear time with sustained visual acuity from 5-6 hours to greater than 15 hours. The treatment also improved the ease of insertion and removal of the contact lenses. After 2 years of treatment, the benefits of progesterone dermal application persisted for at least 3 days without treatment. There was no effect of the progesterone on her tremor symptoms.

After allowing for washout of progesterone for 3 days, she began forehead application of 0.5-0.75 mg dronabinol once daily at night. Initially, the dronabinol had a similar effect to progesterone respecting contact lens wear. The dronabinol treatment was continued for 2 weeks without impacting her symptoms of hand tremor.

The dronabinol administration regimen was altered by dividing equally the once daily dose of 0.5-0.75 mg dronabinol between the conchae of the left ear, the conchae of the right ear, and the forehead. Unexpectedly, by the fourth day of this treatment regimen, the subject realized the hand tremor had noticeably reduced, with a concomitant increase in both function and feel. Comfortable contact lens wear, with ease of insertion and removal, and visual acuity extends for 15 hours or more after dronabinol application.

The subject ceased applying the dronabinol for 3 days and found that the tremor returned in the right hand, although the tremor amplitude was about 50% of pre-treatment level.

She commenced applying progesterone 0.5% to the concha of both ears and her hand tremor has subsided to the same degree as it did with dronabinol treatment to the ears and forehead. Contact lens comfort wear duration was greater than 15 hours.

Over the past 12 months leading up to August 2017, the subject established a regimen of low dose progesterone 1% to the forehead only for daily effective treatment of contact lens discomfort, which provided 15 hours of comfortable wear plus ease of insertion and removal.

The subject has shown no adverse events with neural delivery of low dose progesterone over the course of 3 years. A routine mammography, as well as her serum hormone levels, was normal.

During dronabinol treatment, the subject saw an 80% reduction in essential tremor from the pre-treatment baseline. Due to an unwanted increase in appetite, the subject discontinued the low dose topical dronabinol treatment and was satisfied with a stable new baseline of essential tremor about 50% reduced from pre-treatment levels.

In April 2017, the subject, while still being treated with 1% progesterone applied to the forehead, instituted a once-daily low dose topical testosterone applied to the forehead and ear conchae to determine if doing so would produce a beneficial impact on further tremor reduction and in particular essential tremor triggered by caffeine consumption. Throughout a 4-week treatment with topical testosterone, she noted a further reduction in tremor in amplitude and frequency, as much as a 90% reduction over the original baseline and, surprisingly, a near complete resolution of the caffeine trigger. She stopped the treatment to assess whether the tremor would return to pre-testosterone treatment levels. As of August 2017, the subject is without noticeable tremor. The caffeine trigger for tremor onset, which had been recognized throughout all treatments, has not re-appeared since the completion of the 4-week testosterone treatment. The subject continues on low-dose progesterone 1% applied daily to the forehead as the only treatment.

Example 8

Herpes Ophthalmicus and Herpes Keratitis

A 70-year-old male patient experienced an episode of herpes ophthalmicus and herpes keratitis in September 2003, resulting in thinning melt of the left cornea, loss of vision, inflammation, neuralgia, and a rash of blisters to the left forehead, upper nose, and temple with a subsequent full left-face palsy droop, which required multiple cosmetic surgical procedures to provide some symmetry to the face and partial closure to the eyelids of the left eye.

No corneal graft to the left eye could be attempted due to recurrent thinning of the full cornea and inflammation of the vasculature. The patient was treated with ophthalmic prednisolone, topical and systemic antivirals, topical antibiotics, bandage lens, punctal plugs, and over-the-counter artificial tears and gels. This treatment regimen was continued until January 2011 when the cornea thinned to probable melt-through, necessitating corneal patch surgery. Just prior to the surgery, the patient's vision was measured at 20/2000, or finger vision.

The patient started applying 1% progesterone to his forehead twice daily just before corneal patch surgery planned for January 2011. The dose of progesterone was approximately 1 mg per application. The surgery was avoided as the corneal thinning stabilized but there was no functional vision due to vascular incursion and opacity. The progesterone treatment continued over two years without corneal melt-through.

In September 2014, his corneal tissue had sufficiently epithelialized at the perimeter to attempt a corneal graft, which was successfully completed. Progesterone 1% was applied daily to the forehead post-surgery. Within 9 months vision was restored to best correct vision pinhole 20/50. When using Progesterone 1%, tear film breakup was normal and meibomian glands functioned well.

In February 2015, the patient's visual acuity decreased as a result of the rejection of cells at the lower part of the graft. Moderate central staining continued to persist in a band where eyelids could not close. Intraocular pressure (TOP) in the left eye rose to 22 mmHg. The patient was placed on a treatment regimen that included Prednisolone Forte 6× plus Restasis for rejection 2× daily and oral valacycovir, together with mechanically taping the eyelid closed at night.

In May 2016, the patient initiated a course of twice daily dronabinol treatment, 0.5 mg each dose, to both ears. Through July, stabilization was achieved, and all other medications were discontinued. The staining appeared to improve somewhat, but still moderate; the number of rejected cells became fewer and seemed to be reversing, and TOP started to fluctuate from 22 mmHg, reaching 16 mmHg at a subsequent examination. Visual acuity improved to 20/40.

At the beginning of August, the following surprising findings of signs and symptoms were made by examination: (i) best corrected vision pinhole was 20/25; (ii) TOP was 18 in both eyes; (iii) there was no sign of rejection cells; (iv) corneal graft was completely clear as was the capsule; and (v) staining improved to superficial. The production of filaments had ceased and comfort in the eye and production of tear film normalized. Multiple Keratograph 5M non-invasive tear film break times (NIKBUTs) showed level of 0 (best) with blink interval approximately 24 second, the maximum.

No other episodes of herpes ophthalmicus or herpes keratitis presented.

Valacyclovir and cyclosporine treatments were discontinued in early 2016, and dronabinol treatment was discontinued in August 2016. The patient has been applying Prednisolone infrequently. As of August 2017, there has been no recurrence of Herpes infections and no sign of rejection.

Example 9

Re-establishment of Functional Facial Motor Control in Herpes Facial Palsy

A 70-year-old male had unilateral facial unilateral palsy stemming from 2003 herpes ophthalmicus and herpes keratitis. The left eye lids were unable to close to cover the central cornea without a forceful blink; neither were the lids able to open with the upper lid sagging and without elasticity or muscle control. This static condition was the baseline since the end of 2003 to May 2016, or nearly 13 years.

The left side of the face drooped, the left corner of the mouth drooled, and a noticeable asymmetry presented at rest. The upper lip could only slightly reveal the lowest pat of the upper teeth on the right side. There was minimal functional motor control of facial expression including upper lip. His left side brow, eye lids, cheeks to mouth and chin lacked elasticity and functional motor control, leaving his face fixed, expressionless, and asymmetrical.

Through spring 2016 no changes were seen in the elasticity of the face, asymmetry, motor control or expression, and intermittent episodes of unilateral palsy continued. The facial skin sagged as did the eye lids. The affected left eye lid was partially closed in the resting state, did not close fully, and could only be opened by raising forehead skin. His upper lip was partially frozen on the left side, and drooling was persistent. Lip and mouth expression as in smile was severely restricted.

Beginning in mid-May 2016, the patient began treatment twice daily with dronabinol 2.5 mg in oil, one-third of which was applied equally to the concha of the left ear, to the conchae of the right ear, and to the forehead.

At the beginning of August 2016, 3 months after the start of dronabinol treatment to the ears, the following surprising findings of signs and symptoms were made by examination: The patient had more motor control over both eye lids such that they could be opened and closed naturally. Tear film breakup times improved significantly, reaching level 0 (best) regularly as measured by Keratograph 5M. Visual acuity continued to improve to best corrected vision 20/25 with pinhole. The patient regained control over facial expression muscles from forehead to mouth and lips, and face trended to symmetrical. Early graft rejection diagnosed in May 2016 reversed, persistent central corneal staining resolved to a significant degree, and conjunctival redness improved significantly.

The affected lids gained muscle control and a cumulative effect set in whereby the lids at rest could close and the upper lid achieved the cumulative effect of full muscle control as did the eyelids. The upper lip could be raised and held naturally to expose the whole of the upper teeth and gums. The left side of the face gained elasticity and motor muscle voluntary control. Facial droop and drool improved dramatically at rest.

Dronabinol treatment was discontinued in August 2016. There has been no recurrence of facial palsy to date.

Example 10

Effect of Topical Progesterone on Neural Gene Expression

A study was conducted in a rat model using the same formulation of progesterone and the same route of administration as had been used by the individuals in the preceding examples.

In the study, 7 rats were treated with progesterone 1% on the forehead, estimated to be less than 0.2 mg per dose, and 6 rats received placebo. Two hours later the animals were perfused and brainstems removed. Brainstem tissues were processed for immunohistochemistry using an anti-c-Fos antibody to identify c-Fos protein in cell nuclei that can be counted to assess the activity of c-Fos-positive neurons. Two regions of the spinal trigeminal nucleus were examined: (i) rostral spinal trigeminal nucleus (Vsp) subnucleus interpolaris/subnucleus caudalis (Vi/Vc) region and (ii) caudal Vsp subnucleus caudalis/cervical 1 (Vc/C1) region. The study results showed that rats receiving active product had significantly greater number of activated neurons in the Vi/Vc region but not the Vc/C1 region when compared to rats receiving placebo.

It has been confirmed that secretion of the main tear film components: aqueous by the lacrimal gland, meibum by the Meibomian glands, and mucin by the goblet cells are all neurally regulated. (LeDoux M S et al. 2001; Dartt, D A et al. 2005; Dartt, D A 2009; Meng I D and Kurose M 2013) However this animal study example represents a surprising finding in that a low dose neurosteroid applied to the forehead can stimulate tear film production similar to sensory inputs. Specifically forehead application in the rats signaled the neurons in the Vi/Vc junction of the spinal trigeminal nucleus to activate tear film secretion via the facial nerve and parasympathetic pathways.

The rat model confirmed forehead application of progesterone signaled the neurons responsible for activation of tear film production. Various authors and experiments had confirmed the role of neurons in the rostral subnucleus interpolaris (Vi/Vc) and caudalis (Vc/C1) region of brain stem within the spinal trigeminal nucleus (Vsp), a major termination zone for trigeminal sensory fibers, to innervate the eye. When cFos genes in these neurons are activated, cFos proteins are produced that can be stained to count the number of activated neurons. (Meng et al., 1996; Meng et al., 2013).

Summary and Discussion of Examples

All human examples of neurodegenerative disorder, Parkinson's, essential tremor, herpes ophthalmicus and chronic ocular graft-versus-host disease, had ocular discomfort and signs and symptoms that were treated by low dose progesterone USP, 0.5 to 1 mg per dose, applied in an aqueous formulation to the forehead. Ocular comfort was achieved within a few minutes after application when tear film secretion was also observed, and lasting for at least 12 hours per dose. In the essential tremor example, when progesterone was substituted by low dose dronabinol USP 0.5 mg to 0.75 mg in an oil formulation to the forehead, the same benefits to ocular discomfort was obtained. The afferent nerve accessed is CN V trigeminal nerve but the efferent parasympathetic signaling was via CN VII facial nerve and a branch the greater petrosal nerve that synapses in the pterygopalatine ganglion to innervate tear film secretion. These human examples as well as the animal example confirmed the "cross-talk" between two cranial nerves, i.e. trigeminal CN V and facial CN VII, which enables afferent trigeminal signaling to activate efferent facial CN VII and the parasympathetic ocular system.

In the first Parkinson's example (Example 1), low dose dronabinol USP in an oil formulation when applied to forehead and conchae of the outer ears treated the motor symptoms including tremor and also the non-motor symptoms. Treatment frequency has been twice daily. The forehead signaling follows the same route as described above. The vagus nerve is accessed from conchae of the ear, via the auricular branch of the vagus nerve, the jugular ganglion, then the vagus nerve into the medulla oblongata, part of the brainstem, to the nucleus of the solitary tract, the spinal trigeminal nucleus, nucleus ambiguous, and dorsal motor nucleus. Emanating from this region is the control of multiple vagal functions including respiratory, cardiac, gastrointestinal, and urogenital. The surprising finding was the reduction in almost all the motor symptoms and restoration of cognitive ability within days.

Discontinuation of low dose dronabinol USP to the forehead and conchae of the ear resulted in deterioration of cognition and other non-motor symptoms despite the institution of prescribed medications Azilect (rasagiline) and carbidopa-levodopa. Initiation of testosterone treatment restored improved cognition and other non-motor symptoms.

The second Parkinson's example (Example 2) shows that, in a female diagnosed with Parkinson's who was not taking any prescribed Parkinson's medications, testosterone administration was able to significantly manage both motor and non-motor symptoms of the disease, and showed no disease progression, as assessed by her neurologists. They reported increased strength, energy, and agility.

In the third Parkinson's example (Example 3), low dose progesterone USP treated motor symptoms including tremor and non-motor symptoms when applied to the added conchae region of the outer ears, accessing vagus nerve. The surprising finding was the rapid cessation of tremor within minutes, as well as the sustained effect.

In the essential tremor example (Example 7), the effect of dronabinol applied to the conchae to stop kinetic tremor was first noticed after 3 days although it is possible that resolution was earlier as the results had not been expected. Reduction in benefit that was immediate but transient by coffee drinking also highlighted the cause-effect of dronabinol conchae application.

Low dose testosterone gel topically applied instead of dronabinol induced further reduction in tremor amplitude and frequency. The 4-week treatment with testosterone together with topical progesterone 1% resolved the caffeine trigger for onset of tremor.

Subsequently, a maintenance dose of progesterone 1% applied to the forehead has been sufficient to maintain the subject as tremor-free, and insensitive to the caffeine trigger of tremor onset.

The herpes ophthalmicus/keratitis example (Example 8) is descriptive of the forehead applied progesterone creating a healthy tear film to protect the corneal and conjunctival surface to allow epithelial healing and promote ocular comfort in a viral affected eye, avoiding patch surgery and melt-through. Even more importantly, the reepithelization allowed a corneal graft to be performed years later, to replace the scarred cornea.

In Example 9, what was shown is that over a period of 3 months of dronabinol application to the ear conchae, first a 12-hour dose to dose response which then cumulates into a stable new baseline. This is true simultaneously for the eye, corneal staining, acuity, tear-film production and lid muscle control response normalizing. In the face, droop ad drool significantly resolved; elasticity and facial voluntary motor control improvement is noteworthy, reflected in smiling, lip movement and overall more symmetry. Thus after 13 years, the surprising finding is that persistent functional facial motor control has been achieved to improve the symptoms of unilateral facial palsy. One hypothesis is that afferent signaling is being created and through consequent activated efferent signaling, homeostasis of nerve controls is being restarted and restored utilizing plasticity of the brain.

This is similar to the result seen in the Parkinson's examples where dronabinol and progesterone respectively were applied to the ear conchae regions, with resultant decreased facial masking and more voluntary facial expressions.

Another surprising observation is that the duration of efficacy is at least 12 hours with the easily monitored parameters such as ocular comfort, tear film production, or tremor reduction. This long duration significantly exceeds systemic circulatory half-life of the agents at high dose, <4 hours.

The animal study (Example 10) using a well-known rat model confirmed the activation of neurons in the Vi/Vc region in the spinal trigeminal nucleus of the brainstem that activated tear film production. The model traditionally applied stimuli to the eye itself, such as cornea, to activate tear film secretion. In the specific study low dose progesterone in the same formulation that was used in the clinic was applied to the rat head instead. A significant increase in activated neurons was found in rats receiving progesterone on the forehead as compared to those receiving placebo.

In all the examples cited, the finding is chemical neural cranial stimulation bypasses the blood brain barrier.

There may be some similarities between the chemical nerve stimulation described in this patent and electrical stimulation such as accessing the vagus nerve via its only peripheral branch, the auricular branch of the vagus nerve, and that chemical nerve stimulation likely generates electrical nerve signals similar to direct electrical stimulation. However the similarities end here since nerve signaling created by topical chemical or pharmaceutical nerve stimulation engages the body's own electrochemical system with its endogenous frequency and amplitude. In contrast, direct electrical stimulation in current use would override the body's own electrochemical system, such as with deep brain stimulation, that may give rise to unwanted side effects.

The following references can be used to better understand the background of the invention:

Barnard et al., Neurol. Neurosurg. Psychiatry. 1974 37(11):1259-64.
Benito-León J. et al., Cerebellum. 2016 June; 15(3):253-62.
Calabrese M. et al., Neurology. 2010 Oct. 5; 75(14):1234-40.
Dartt D. A., Ocul Surf. 2004 April; 2(2):76-91.
Dartt D. A., Prog Retin Eye Res. 2009 May; 28(3):155-77.
Dendrou C. A. et al., 2015 Sep. 15; 15(9):545-58.
Farlow M R et al., Up-to-Date 2016 June.
Food and Drug Association. Report 2016 April
Imamura T. et al., Neuroreport. 1999 Jun. 23; 10(9):1903-7.
International Essential Tremor Foundation. Facts about essential tremor. 2012. EssentialTremor.org.
Jellinger K A. J. Neural Transm Suppl. 2002; (62):347-76.
LeDoux M S et al., Invest Ophthalmol Vis Sci. 2001 October; 42(11):2434-41.
Lewy Body Dementia Association. https://www.lbda.org/category/3437/what-is-lbd.htm
Lucchinetti, C F et al., N. Engl. J. Med. 2011 Dec. 8; 365(23): 2188-2197.
Meng I D et al., Neuroscience. 1996 May; 72(1):243-54.
Meng I D et al., Exp Eye Res. 2013 December; 117:79-87.
National Institute of Neurological Disorders and Stroke. Tremor fact sheet. July 2012.
Pandey S et al., Parkinsonism Relat. Disord. 2016 Apr. 1. pii: S1353-8020(16)30078-5.
Popescu B F et al., BMC Neurol. 2012 Mar. 7; 12:11.
Seppi K. et al., Neurology. 2007 Aug. 21; 69(8):717-8.
Richards R G et al., Health Technol Assess. 2002; 6(10): 1-73.
Wichmann T et al., Neurotherapeutics. 2016 April; 13(2): 264-83.
Zouboulis C C. Hormones (Athens). 2004 January-March; 3(1):9-26.

The content of each of the above references is incorporated herein by reference in its entirety.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, a person skilled in the art can easily ascertain the essential characteristics of the present disclosure, and without departing from the spirit and scope thereof, can make various changes and modifications of the present disclosure to adapt it to various usages and conditions. Thus, other embodiments are also within the claims.

The invention claimed is:

1. A method for treating a symptom of a neurodegenerative condition, the method comprising:
   identifying a subject having a symptom of a neurodegenerative condition, and
   administering topically a composition that contains a sex steroid, a cannabinoid, or a combination thereof to an area of the forehead and to the outer ear of the subject not including the ear canal,
wherein the sex steroid is progesterone or testosterone and the condition is essential tremor, Parkinson's tremor, ocular graft-versus-host-disease, or herpes facial palsy.

2. The method of claim 1, wherein the forehead includes an area of the head bounded by the hairline, above the supraorbital ridge, and the temporal ridges.

3. The method of claim 1, wherein the area of the outer ear is the concha cymba, concha cavum, antihelix, crus helix, crura of antihelix, intertragal notch, and the dorsal surface of the auricle.

4. The method of claim 1, wherein administering the composition provides a dose of 0.001 mg to 30 mg per day of the sex steroid.

5. The method of claim 1, wherein administering the composition provides a dose of 0.001 mg to 10 mg per day of the cannabinoid.

6. The method of claim 5, wherein the cannabinoid is selected from the group consisting of dronabinol, cannabinol, cannabidiol, Δ9-tetrahydrocannabinol, Δ8-tetrahydrocannabinol, 11-hydroxy-tetrahydrocannabinol, 11-hydroxy-Δ9-tetrahydrocannabinol, levonantradol, Δ11-tetrahydrocannabinol, tetrahydrocannabivarin, anandamide, virodhamine, noladin ester, 2-arachidonoylglycerol, and nabilone.

7. The method of claim 6, wherein the cannabinoid is dronabinol or Δ9-tetrahydrocannabinol.

8. The method of claim 1, wherein administering the composition provides a dose of 0.001 mg to 30 mg per day of the sex steroid and 0.001 mg to 10 mg per day of the cannabinoid.

9. The method of claim 8, wherein the cannabinoid is dronabinol or Δ9-tetrahydrocannabinol.

10. The method of claim 1, wherein the cannabinoid is dronabinol or Δ9-tetrahydrocannabinol.

11. The method of claim 1, wherein the subject is already undergoing pharmacological, surgical, electrical stimulation, acupuncture, or ultrasound treatment for the neurodegenerative condition.

12. The method of claim 1, wherein topically administering the composition retards progression of the neurodegenerative condition.

13. The method of claim 1, wherein the composition is a pharmaceutical preparation in the form of a gel, a suspension, a cream, a liquid, an ointment, or a transdermal patch.

14. The method of claim 1, wherein the composition is effective for treating the symptom for at least 8 hours after a single administration.

15. The method of claim 1, further comprising providing electrical stimulation to the area of the outer ear, wherein the composition enhances efficacy of the electrical stimulation.

16. The method of claim 3, wherein the area of the outer ear is the concha cymba or the concha cavum.

* * * * *